(12) United States Patent
Kitajima

(10) Patent No.: US 6,962,819 B1
(45) Date of Patent: Nov. 8, 2005

(54) METHOD OF MEASURING ANALYTE USING DRY ANALYTICAL ELEMENT

(75) Inventor: Masao Kitajima, Saitama (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 08/407,807

(22) Filed: Mar. 20, 1995

Related U.S. Application Data (63) Continuation of application No. 07/917,825, filed on Jul. 21, 1992, now abandoned.

(30) Foreign Application Priority Data

| | | |
|---|---|---|
| Jul. 22, 1991 | (JP) | 3/204545 |
| Mar. 16, 1992 | (JP) | 4/58484 |

(51) Int. Cl.$^7$ .......................................... G01N 21/77
(52) U.S. Cl. .................. 436/170; 436/166; 436/169; 436/176; 436/177; 436/178; 422/56; 422/57; 422/58
(58) Field of Search ............ 422/56–58; 436/169–170, 436/177–178, 46, 86, 166

(56) References Cited

U.S. PATENT DOCUMENTS

| | | | | |
|---|---|---|---|---|
| 2,710,688 | A | * | 6/1955 | Drey .................... 422/102 X |
| 3,607,090 | A | * | 9/1971 | Maxon .................... 422/66 |
| 3,992,158 | A | * | 11/1976 | Przybylowicz et al. ....... 422/56 |
| 4,144,306 | A | * | 3/1979 | Figueras .................... 422/56 |
| 4,178,153 | A | * | 12/1979 | Sodickson ................ 422/56 X |
| 4,327,073 | A | * | 4/1982 | Huang .................... 436/44 |
| 4,839,296 | A | * | 6/1989 | Kennedy et al. ............ 436/170 |
| 5,064,766 | A | * | 11/1991 | Wardlaw et al. .......... 422/56 X |
| 5,336,599 | A | * | 8/1994 | Kitajima .................... 435/15 |

FOREIGN PATENT DOCUMENTS

| | | | |
|---|---|---|---|
| DE | 217897 | * | 1/1985 |
| EP | 0022377 | | 1/1981 |
| EP | 0166365 | | 1/1986 |
| EP | 0436897 | | 7/1991 |
| GB | 2052057 | | 1/1981 |
| JP | 1-107136 | * | 4/1989 |
| JP | 3-289543 | * | 12/1991 |
| WO | 8702267 | | 4/1987 |

* cited by examiner

Primary Examiner—A Soderquist
(74) Attorney, Agent, or Firm—Reed Smith LLP

(57) ABSTRACT

A method of measuring an analyte using a dry analytical element which comprises, a process of supplying a measuring reagent solution to the anlaytical element comprising at least a hydrophilic polymer layer and a microporous layer having a surface rendered hydrophilic and having a blood cell-separating ability laminated onto a water-impermeable support and not containing the measuring reagents to which a liquid sample has been supplied and thereby reaction occuring, and a process of measuring the analytical element wherein the reaction occurred by an optical means. According the above method, the shelf life of the analytical element is greatly improved. Besides, since the measuring reagnts used in the conventional wet analysis can be used, it is not necessary to develop analytical elements for each measuring item. Moreover, one kind of analytical element can be applied to many items.

18 Claims, 3 Drawing Sheets

METHOD OF MEASURING ANALYTE USING DRY ANALYTICAL ELEMENT

RELATED APPLICATIONS

This application is a continuation of application Ser. No. 07/917,825, filed Jul. 21, 1992, now abandoned.

BACKGROUND OF THE INVENTION

This invention relates to a method of measuring an analyte in a liquid sample using a dry analytical element which does not contain reagents capable of reacting directly with the analyte to produce a measurable change.

It has been conducted from long ago to diagnose human diseases by analyzing blood, urine or the like.

As a method therefor, there is the wet analysis using a solution reagent. This method has a long history, and various detecting reagents have been developed for many items. Various analyzers have also been developed which range from compact apparatuses to big scale apparatuses. Samples used for the wet analysis are plasma, serum, urine and the like, but whole blood samples are in general not used as it is.

In the wet analysis, reagents can be divided into several groups by considering their stability during stock, and dissolved and mixed at the time of use. It is also possible to divide the addition of respective reagents into several steps.

Moreover, since it is possible co prepare a suitable amount of each reagent by dissolving according to the number of samples to be measured, the measuring cost per one sample is reduced. It is troublesome to automate the measurement by combining the treatment of many solutions. However, there is a history to develop clinical analytical apparatuses, and various automatic apparatuses having a good efficiency have already been developed and put to practical use in every field requiring big, middle, small treating capacity according to great social requirement.

Disadvantages of the wet analysis are in the preparation and supply of samples. Since this method is composed on the premise of the measurement of transmitted light through a transparent solution, whole blood samples cannot be used as the samples to be measured without pretreatment. That is, after drawing whole blood samples, they are centrifuged, and the plasma or serum which is the supernatant is put into a sample cup, or the centrifuge tube as it is set in a measuring apparatus instead of the sample cup. In addition to the complexity in the above operations, there is a further problem that it is necessary to keep a great amount of whole blood samples for separating a sufficient amount of plasma or serum without contamination of red blood cells.

In order to obtain 200 $\mu$l of a plasma sample by centrifuging, usually, 1.5 to 2 ml of whole blood is necessary. Even though centrifuging and aftertreatment are conducted carefully, a minimum amount of whole blood is estimated to be about 500 $\mu$l.

On the other hand, a necessary amount of a sample is about 10 $\mu$l per one analytical item for the measurement, and accordingly, it is only 100 $\mu$l for 10 items and 200 $\mu$l for 20 items. Nevertheless, 2 to 20 ml of blood is actually drawn in hospitals or the like, that is, 50 to 100 times as much as the necessary plasma amount is drawn. Every person, even a healthy person, suffers with pain mentally and physically by inserting the needle of a syringe into blood tube and drawing blood. Particularly, persons having thin tubes constitutionally and sick persons suffer with pain accompanied with drawing beyond imagination, and patients who are repeatedly drawn greatly desire to reduce the amount of blood drawn to a minimum.

Incidentally, in the blood drawing room of hospitals, medical practitioners and clinics, whole blood samples drawn and put into a tube or a vacuum syringe are transported as it is or in cooled conditions to a central assay room or an assay center. That is, each blood sample is centrifuged after transportation, and separated into solid components such as red blood cells and plasma or serum which is used as the analytical sample. During the transportation, there is a possibility that biochemical reactions affecting the analysis proceed by the coexistance of red blood cells, but countermeasures are taken only against the variation factors which are known to affect analytical results remarkably great, such as inhibition to glycolysis and anticoagulation.

By taking the above matters into consideration, it is preferred that centrifuging is conducted immediately after blood drawing, but this is usually not done. Because, analytical methods using blood serum as the sample have been established historically, and it is necessary for the separation of serum to complete coagulation by leaving at least for 30 minutes to 1 hour. Moreover, when blood is centrifuged after adding an anticoagulant, according to samples, fibrins occasionally deposit between the centrifugation and the measurement by an analyzer. The above matters are liable to induce troubles in the transferring system, such as pipetting syringe or tubes in the analyzer.

Accordingly, it is desirable to obtain serum samples by centrifuging within about 1 hour after drawing blood. However, although it is possible in the assay in hospitals, in the case of assay centers requiring a time for the transportation of samples, the time when centrifuging is conducted quite varies, and the centrifuging is often conducted after one day or more.

As an analytical method which has conquered the disadvantages accompanied with the preparation and supply of samples, many dry analytical elements (also called analytical film, multilayer test strip, or the like) have been developed wherein all reagents necessary for qualitative or quantitative analysis are incorporated into a test paper or an analytical element such as multilayer anlaytical film, and are sold.

The dry analytical elements have the following characteristics.
1) All reagents necessary for analysis are incorporated into an analytical element.
2) Reactions necessary for analysis occur merely by spotting a sample (usually, plasma, serum or urine, as to partial items, whole blood).

The dry analytical elements are roughly divided into 3 groups according co their utilization field.
Group 1: The object is in screening by practitioners and at homes, and the results can be judged qualitatively (+/−) or semiquantitatively (about 5 degrees) by visual inspection.
Group 2: Measuring place can be relatively freely selected by combining an analyzer characterized by compact size and simple operation. Used in emergency assay rooms, childhood wards, practitioners, small scale hospitals, etc.
Group 3: Used for measuring routine assays in hospitals or assay centers using a fully automatic analyzer.

The construction and content of the anlaytical elements are different according to the above classification.

Representative anlaytical elements belonging to Group 1 are urine test paper and blood sugar test paper. Analytical operations of these papers are simple, and analyzer is not necessary. However, the results are rough (such as normal or abnormal), and it is premised that, in the necessary case, sample is measured again by another analytical means capable of obtaining a quantitative result.

In the anlaytical elements according to this method, operations by a specialist, such as clinical assay engineer, medical doctor and nurse, are not premised, and commonly, it is composed so that urine or whole blood can be used as a sample without any pretreatment.

The object of the analytical elements belonging to Group 2 is in quantitative analysis, and quantitative measurement by an apparatus is premised. Operation is relatively simple, although it is not simpler than Group 1, a specialyst such as a clinical assay engineer is not premised. As to samples, analytical elements to which anyone of whole blood, plasma, serum or wrine is applicable have gradually been developed, but analytical items measurable by whole blood are still 10 and several items which are relatively restricted.

The samples applicable to fully automatic analyzers in Group 3 are, in general, limited to plasma, serum and urine, and whole blood cannot be used as the sample. However, measurable items have gradually been increased, and analytical elements have already been developed for measuring at least 40 items.

However, in the dry anlaytical elements, all reagents necessary for reactions must be incorporated into the analytical element; Nevertheless, the characterics of the reagents are different respectively according to analytical items, and as a result, there is a great problem that much labor, time and equipment cost are consumed by developing recipe and optimizing manufacturing conditions.

Besides, since all reagents are contained, it is necessary to keep sufficiently dry conditions for the stock of the analytical elements for a long period. For that purpose, usually, each analytical element is packed by a moisture proof package, and if necessary, a drying agent is put in the package.

Even when the dry package and cooling preservation are employed, shelf life is only 1 to 2 years which elevates the price of the dry analytical elements.

SUMMARY OF THE INVENTION

An object of the invention is to provide a method of measuring an analyte capable of providing an accurate result by a simple operation using a dry analytical element which can be prepared in a simple process, which can be preserved for a long period, and which can use a very small amount of a body fluid, such as whole blood, plasma, serum or urine, as the sample.

Another object of the invention is to provide a method of preserving and transporting an analytical element, to which a body fluid such as blood, a biological sample or an aqueous solution sample is supplied, with keeping a sufficient anlaytical accuracy.

Another object of the invention is to provide a method capable of measuring an analytical element supplied with a sample and then preserved, even in the case that a rate assay is necessary, such as enzyme reaction.

Another object of the invention is to provide a dry analytical element used in the above methods.

The present invention provides methods of measuring an analyte using a dry analytical element which have achieved the above objects, which comprises, a process of supplying a measuring reagent solution to the analytical element comprising at least a hydrophilic polymer layer and a microporous layer having a surface rendered hydrophilic and having a blood cell-separating ability laminated onto a water-impermeable support and not containing the measuring reagents co which a liquid sample has been supplied and thereby reaction occuring, and a process of measuring the analytical element wherein the reaction occurred by an optical means.

In the above analytical element not containing the measuring reagents, a water-impermeable gas-permeable layer and/or a light-shielding layer may be provided between the hydrophilic polymer layer and the microporous layer.

In the above analytical element not containing the measuring reagents, the microporous layer having a surface rendered hydrophilic and having a blood cell-separating ability has both functions of a blood cell filtering layer and a spreading layer, but a spreading layer may be provided adjacent to the microporous layer.

In the above method, the microporous layer may be removed before or after allowing reaction to occur by supplying the measuring reagent solution to the analytical element which has been dried. Thereby, measurement can be conducted by either of the reflection method or the transmission method, even when whole blood is used as the liquid sample.

Besides, in the case that the microporous layer is removed from the dried analytical element before the supply of the measuring reagents, a layer having spreading ability (the microporous layer or a spreading layer described later) may be provided again. This method is effective in the case that the spreading ability of the microporous layer is degraded by using a whole blood sample.

DETAILED DESCRIPTION OF THE INVENTION

An embodiment of the analytical element has the fundamental construction composed of the hydrophilic polymer layer, a porous spreading layer and the microporous layer having a surface rendered hydrophilic and having a blood cell-separating ability laminated on the water-impermeable support.

The microporous layer may be in either of a substantially unseparable state or a separable state after the supply of the liquid sample, called partial adhesion described later, from the porous spreading layer.

The microporous layer specifically separates blood cells and plasma from whole blood without hemolysis to the degree substantially not affecting the analytical values.

Although the blood cell-blood plasma separation mechanism is not clear, it is thought that the microporous layer does not trap blood cells only by the surface, but catches to remove blood cells gradually by entangling at first large blood cell components and then smaller blood cell components in the space structure with permeating in the thickness direction in total of the microporous layer composed of fluorine-containing polymer and the porous spreading layer, called the volumetric filtration.

As the microporous layer having a blood cell-separating ability of which the surface is rendered hydrophilic, fluorine-containing polymers, polysulfones and the like of which the surface is rendered hydrophilic can be used.

The fluorine-containing polymers include polyvinylidene fluoride, polytetrafluoroethylene and so on, and polytetrafluoroethylene is preferred. The pore size of the microporous layer formed of fluorine-containing polymer is usually in the range of about 0.2 µm to about 60 µm, preferably about 1 µm to about 20 µm, more preferably about 1 µm to about 10 µm, and the void content is usually in the range of about 40% to about 95%, preferably about 50% to about 80%. The layer thickness is usually about 10 µm to about 200 µm, preferably about 30 µm to about 150 µm, and about 50 µm to about 120 µm is the most preferable by considering handling, such as the occurrence of wrinkling in the manufacturing process. The adhesive strength of adhesive used for the partial adhesion to the adjacent porous spreading layer can be strengthened by providing the physical activation (preferably glow discharge or corona discharge) disclosed in U.S. Pat. No. 4,783,315 on at least one side of the microporous layer of fluorine-containing polymer to render hydrophilic. As the fluorine-containing polymer sheets usable as the microporous layer, there are the microporous matrix layer (microporous layer) composed of polytetrafluoroethylene fibrils (fine fibers) disclosed in WO 87/02267, Gore-Tex (W. L. Gore and Associates), Zitex (Norton), Poreflon (Sumitomo Denko), etc. The pore size (micropore size) is about 0.1 µm to about 50 µm, and the layer thickness is about 20 to about 400 µm. As the structure, there are unnstretched one, uniaxially stretched one, biaxially stretched one, nonlaminated single layer type, laminated double layer type, such as a membrane laminated to another membrane structure such as a fiber membrane. Other fluorine-containing polymer sheets usable as the microporous layer include polytetrafluoroethylene microporous membranes disclosed in U.S. Pat. No. 3,368,872 (Examples 3 and 4), U.S. Pat. No. 3,260,413 (Examples 3 and 4), U.S. Pat. No. 4,201,548, etc., polyvinylidenefluoride microporous membranes disclosed in U.S. Pat. No. 3,649,505 and the like. Among the above fluorine-containing polymer microporous membranes, particularly suitable membranes for the microporous layer constructing the blood cell filtering layer are those having a small pore size which substantially does not pass red blood cells, a thin thickness and a great void content. Actually, preferred membranes have a pore size of 1 to 10 µm, a membrane thickness of 10 to 200 µm and a void content of more than 70%. In the case of nonlaminated type microporous membrane having fibril structure or having been uniaxially or biaxially stretched, microporous membrane having a great void content and a short filtering pass can be prepared by stretching. In microporous membranes having a short filtering pass, clogging rarely occurs by solid components (mainly red blood cells) in blood, and the separation time of blood cells and plasma is short. As a result, accuracy in quantitative analysis is improved. The microporous membrane of fluorine-containing polymer may be prepared by using a single fluorine-containing polymer or blending two or more kinds of fluorine-containing polymers or further blending one or more polymers not containing fluorine or fibers therewith.

It is well known that fluorine-containing polymer microporous membranes as it is have a low surface tension. As a result, when the membrane is used as the blood cell filtering layer, aqueous liquid samples are repelled and do not diffuse nor permeate over the surface or into the inside. In the analytical element of the invention, the above repelling problem has been resolved by incorporating a sufficient amount of surfactant for rendering the outer surface and the inner space surface of the fluorine-containing polymer microporous membrane substantially hydrophilic thereinto. In order to impart a hydrophilic property sufficient for diffusing, permeating or moving an aqueous liquid sample over the surface or into the inside of the fluorine-containing polymer microporous membrane without repelling to the membrane, in general, it is necessary that the space surface of the membrane is coated with a surfactant in an amount of about 0.01 to 10%, preferably about 0.1 to 5%, more preferably about 0.1 to 1% of the void volume of the membrane. For example, in the case of a fluorine-containing polymer microporous membrane 50 µm in thickness, a preferred amount of surfactant to be impregnated is usually in the range of 0.05 to 2.5 g/m². As the method of impregnating surfactant into a fluorine-containing microporous membrane, a common method comprises immersing the fluorine-containing microporous membrane in the surfactant solution dissolved in a low boiling point (a preferable boiling point is in the range of about 50° C. to about 120° C.) organic solvent (e.g. alcohols, esters, ketones) to permeate into the inner spaces of the membrane substantially sufficiently, taking the membrane out of the solution slowly, and then drying by blowing air (preferably warm air). The surfactant may be incorporated into the fluorine-containing polymer microporous membrane together with other components such as pretreatment reagents for the microporous membrane constructing a blood cell filtering layer.

As the surfactant for rendering the fluorine-containing polymer microporous membrane hydrophilic, the surfactant may be nonionic, anionic, cationic or ampholytic. However, nonionic surfactants are advantageous for the multilayer analytical elements for analyzing whole blood samples, because nonionic surfactants have a relatively low hemolytic activity among the above surfactants. Suitable nonionic surfactants include alkylphenoxypolyethoxyethanol, aklylpolyether alcohol, polyethyleneglycol monoester, polyethyleneglycol diester, higher alcohol-ethylene oxide adduct (condensate), polyol ester-ethylene oxide adduct (condensate), higher fatty acid alkanol amide, etc. Examples of the nonionic surfactant are as follows: As the alkylphenoxypolyethoxyethanol, there are isooctylphenoxypolyethoxyethanols (Triton X-100; containing 9–10 hydroxyethylene units on average, Triton X-45; containing 5 hydroxyethylene units on average) and nonylphen xypolyethoxyethanols (IGBPAL C0-630; containing 9 hydroxyethylene units on average, IGBPAL CO-710; containing 10–11 hydroxyethylene units on average). As the alkylpolyether alcohol, there are higher alcohol polyxoyethylene ethers (Triton X-67; CA Registry No. 59030-15-8), etc.

The fluorine-containing polymer microporous membrane may be rendered hydrophilic by providing one or more water-insolubilized water-soluble polymers in its porous spaces. The water-soluble polymers include oxygen-containing hydro carbons, such as polyvinyl alcohol, polyethylene oxide, polyethylene glycol, methyl cellulose, ethyl cellulose, hydroxyethyl cellulose and hydroxypropyl cellulose, nitrogen-containing ones, such as polyacrylamide, polyvinylpyrrolidone, polyvinylamine and polyethylenemine, negative charge-containing ones, such as polyacrylic acid, polymetacrylic acid and polystyrene sulfonic acid, and the like. The water-insolubilization may be conducted by heat treatment, acetal-inducing treatment, esterification, chemical reaction by potassium dichromate, crosslinking by ionizable radiation, or the like, Details are disclosed in Japanese Patent KOKOKU Nos. 56-2094 and 56-16187.

The polysulfone microporous membrane can be prepared by dissolving polysulfone into dioxane, tetrahydrofuran, dimethylformamide, dimethylacetamide, N-methyl-2-pyrrolidone or a mixed solvent thereof to obtain a raw liquid for forming film, casting into film by flowing directly into a coagulating solution, washing, and then drying. Details are disclosed in Japanese Patent KOKAI No. 62-27006. In addition, polysulfone microporous membranes are also disclosed in Japanese Patent KOKAI Nos. 56-12640, 56-86941, 56-154051, etc., and they are applicable to the invention. The polysulfone microporous membrane can be rendered hydrophilic, similar to the fluorine-containing polymer, by incorporating surfactant or providing water-insolubilized water-soluble polymer.

The spreading layer has a function to spread components contained in an aqueous liquid sample in plane without uneven distribution and to supply them to the hydrophilic polymer layer at a constant rate per an unit area, and may be composed of every nonfibrous or fibrous porous materiel known for the spreading layer of conventional dry analytical elements. Examples of the spreading layer includes nonporous isotropic microporous medium layers represented by membrane filter (blushed polymer) disclosed in U.S. Pat. No. 3,992,158, nonfibrous porous layers represented by continuous space-containing three dimensional lattice grain structure layer where polymer particulates are joined at spots by a water-nonswelling adhesive disclosed in U.S. Pat. No. 4,258,001, porous layers composed of woven fabric disclosed in U.S. Pat. No. 4,292,272, CB 2,087,074A, etc., porous layers composed of knitted fabric disclosed in EP 0,162,302A, various filter papers and the like.

The spreading layer may be composed of two or more microporous layers as disclosed in EP 0,166,365A, EP 0,226,465A, etc. As to th multilayer analytical element wherein two or more porous layers are superposed, it is necessary to have the construction that all layers are integrally laminated at the time of sample spotting, but it is not necessary to be integrated in the subsequent processes. Optionally, the anlaytical element can be used in the state that the first spreading layer is separated from the second spreading layer.

The spreading layer may contain a nonionic, anionic, cationic or ampholytic surfactant in order to accelerate spreading of a sample. Besides, it may contain a spreading controller, such as hydrophilic polymer for the purpose of controlling spreading. Furthermore, it may contain all or a part of various reagents for accelerating the object detecting reaction or reducing or inhibiting interfering reactions.

A suitable thickness of the spreading layer is 20 to 200 $\mu$m, preferably 50 to 170 $\mu$m, more preferably 80 to 150 $\mu$m.

The hydrophilic polymer layer may be composed of various known polymers which are water-soluble, swellable and hydrophilic and are used for conventional dry analytical elements. The hydrophilic polymer is generally a natural or synthetic hydrophilic polymer having a swelling ratio in the range of about 1.5 to about 20 times preferably from about 2.5 to about 15 times at water absorption at 30° C. Examples of the hydrophilic polymer are gelatines, such as acid-treated gelatin and deionized gelatin, gelatin derivatives, such as phthalated gelatin and hydroxyacrylate-graft gelatin, agarose, pullulan, pullulan derivatives, polyacrylamide, polyvinyl alcohol and polyvinylpyrrolidone. Instead of the hydrophilic polymer layer, paper or porous polymer membrane having hydrophilic surface can be used.

A suitable thickness of the hydrophilic polymer layer is about 1 to 100 $\mu$m, preferably about 3 to 50 $\mu$m, more preferably about 5 to 30 $\mu$m. It is preferred that the hydrophilic layer is substantially transparent. The hydrophilic polymer layer may contain all or a part of various reagents for accelerating the object detecting reaction or reducing or inhibiting interfering reactions.

The water-impermeable support may be a known water-impermeable support used in conventional dry analytical elements, and includes a transparent film made of polyethylene terephthalate, polycarbonate of bisphenol A, polystyrene, cellulose ester, such as, cellulose diacetate, cellulose triacetate or cellulose acetate propionate, or the like. The thickness of the support is usually in the range of about 50 $\mu$m to about 1 mm, preferably from about 80 $\mu$m to about 300 $\mu$m. The support is usually light-transmissive, but in the case of measuring from the spreading layer side, it may be colored or may be opaque. The support may be provided with an undercoating layer on its surface in order to strengthen the adhesion of the hydrophilic polymer layer.

Herein, the partial adhesion (porous adhesion) is explained of the microporous layer formed of fluorine-containing polymer containing surfactant to the porous sperading layer which is a characteristic of the dry analytical element used in the invention. The partial adhesion is a form of adhesion between 2 porous layers or a porous layer and a nonporous layer adjacent to each other disclosed in EP 0,166,365 A, EP 0,226,465 A, etc., and it is an adhesion where 2 adjacent layers are substantially closely joined and integrated by adhesive disposed partially or intermittently at their interface and arranged so that uniform passage of liquid is substantially not inhibited at the 2 faces adjacent to each other and the space therebetween.

In the analytical element used in the invention, the interface between the microporous layer formed of fluorine-containing polymer and the porous spreading layer may be joined by the partial adhesion (porous adhesion). A usual adhesion method comprises disposing adhesive partially onto the porous spreading layer, and subsequently joining the microporous layer formed of fluorine-containing polymer with pressing uniformly and lightly. Conversely, the adhesion may be conducted so that adhesive is partially disposed onto the microporous layer, and then, the porous spreading layer is joined thereonto with uniform light pressing. Furthermore, it is also possible that adhesive is partially disposed onto a microporous sheet material which is used as the porous spreading layer and subsequently the microporous layer formed of fluorine-containing polymer is joined thereonto with uniform light pressing, or conversely, that adhesive is partially disposed onto the microporous layer formed of fluorine-containing polymer and subsequently a microporous sheet material which is used as the porous spreading layer is joined thereonto with uniform light pressing. Thereafter, the porous sheet material which is used as the spreading layer is uniformly laminated onto the hydrophilic polymer layer. As the method of disposing adhesive partially onto the microposous layer formed of fluorine-containing polymer or the porous spreading layer, it may be conducted according to the method disclosed in Japanese Patent KOKAI Nos. 61-4959, 62-138, 756, DE 3,721,236 A, etc. Among the above various methods, the printing method is preferred. In the printing method, the process of transferring to adhere adhesive to a porous layer or a detecting function layer using a printing plate roller (gravure printing plate or intaglio printing plate is preferred) and the process of joining adjacent two layers can be conducted, for example, by using a known apparatus and method disclosed in Ed. Japan Printing Society, "Insatsu Kogaku Binran (Printing Engineering Handbook)", pp 839–853, Kihodo Shuppan, Tokyo, 1983, etc.

The adhesives applicable are disclosed in Japanese Patent KOKAI No. 62-138756, the above "Insatsu Kogaku Binran", pp 839–853, etc. The adhesive may be in water solvent type, organic solvent type or thermal adhesion (or heat-sensitive) type. As the water solvent type adhesive, there are aqueous pastes, such as starch paste, aqueous solutions of dextrin, carboxymethyl cellulose, polyvinyl alcohol, etc., and vinyl acetate-butyl acrylate copolymer emulsion. As the organic solvent type adhesive, those having a slow evaporation speed of the solvent are suitable. Thermal adhesion (or heat-sensitive) type adhesives are particularly useful. As the hot-melt type adhesives in thermal adhesive (or heat-sensitive) type, the hot-melt type adhesives disclosed in "Kogyo Zairyo (Industrial Materials)", vol. 26 (No. 11), pp 4–5 are usable. Examples are ethylene copolymers, such as ethylene-vinyl acetate copolymer, ethylene-ethyl acrylate copolymer and ethylene-acrylic acid copolymer, polyolefins, such as low molecular weight polyethylene or atactic polypropylene, polyamides, such as nylon, thermoplastic rubbers, such as SBS and other styrene block copolymers, styrene-butadiene rubber, butyl rubber, urethane rubber, rosin, petroleum resin, terpere resin, and synthetic wax. Among them, silicone group, acrylic group and phenol group pressure-sensitive adhesives are particularly useful for the invention.

In the embodiment that the microporous layer formed of fluorine-containing polymer is separated after the spotting of a sample, the microporous layer is not necessary to be joined to the spreading layer, and it is sufficient that the microporous layer is superposed so that th diffusion and permeation of the sample proceed quantitatively.

In the method of the invention, the analyte to be measured is not limited, and any analyte usually measured in clinical assay field of which the analytical method has already established can be measured, such as enzymes, lipids, inorganic ions, metabolites, proteins, various components derived from living body, such as globulins, antigens and antibodies, medicines, hormones and tumor markers.

The dry analytical element used in the invention may have various constructions described below according to the analytical item or the sample to be measured. Some fundamental layer constructions are shown in FIGS. 1–8.

In the figures, 1 indicates blood cell filtering layer, 2 indicates spreading layer, 3 indicates hydrophilic polymer layer, 4 indicates support, 5 indicates reflecting layer, 6 indicates barrier layer, 7 indicates mordant layer, and 8 indicates blood cell filtering spreading layer.

1. Analytical Element having a Layer Construction of Water-impermeable Support/Hydrophilic Polymer Layer/Spreading Layer/Microporous Layer Formed of Fluorine-containing Polymer Containing Surfactant:

This analytical element is effective for the analysis of Ca, COT (glutamic-oxaloacetic transaminase), GPT (glutamic-pyruvic transaminase), Γ-GTP (Γ-glutamyl transpeptidase), glucose, LDH (lactate dehydrogenase), CPK (creatine phosphokinase), TP (total protein), Alb (albumin), Tcho (total cholesterol), UA (uric acid), neutral fats, etc.

2. Analytical Element having a Layer Construction of Water-impermeable Support/Hydrophilic Polymer Layer/Spreading Layer and Containing Chromogen in Hydrophilic Polymer Layer and/or Spreading Layer/Microporous Layer Formed of Fluorine-containing Polymer Containing Surfactant:

The chromogen applicable to the invention includes 4-aminoantipyrines (synonym: 4-aminophenazone, i.e. 1-phenyl-2,3-dimethyl-4-amino-3-pyrazoline-5-one) disclosed in Ann, Clin. Biochem., 6, 24–27 (1969), and 4-aminoantipyrine analogs, such as tri-substituted-4-amino-3-pyrazoline-5-one such as 1-(2,4,6-trichlorophenyl)-2,3-dimethyl-4-amino-3-pyrazoline-5-one and 1-(3,5-dichloropheynyl)-2,3-dimethyl-4-amino-3-pyrazoline-5-one disclosed in EP 0,103,901A, and 1-phenyl-2,3-dimethyl-4-dimethylamino-3-pyrazoline-5-one disclosed in U.S. Pat. No. 3,886,045. Preferred compounds are 4-aminoantipyrine, 1-(2,4,6-trichlorophenyl)-2,3-dimethyl-4-amino-3-pyrazoline-5-one, 1-(3,5-dichlorophenyl)-2,3-dimethyl-4-amino-3-pyrazoline-5-one, and the like.

3. Analytical Element having a Layer Construction of Water-impermeable Support/Hydrophilic Polymer Layer/Spreading Layer/Microporous Layer Formed of Fluorine-containing Polymer Containing Surfactant and Containing Chromogen and Other Reagents (Excluding the Measuring Reagent Described Later) in Hydrophilic Polymer Layer and/or Spreading Layer;

Examples of the other reagents are POP (peroxidase)) NAD (nicotinamide adenine dinucleotide), NADP (nicotinamide adenine dinucleotide phosphate), DIP (diaphorase), etc.

In the above constructions of 2 and 3, the chromogen and the ocher reagents can be supplied after a liquid sample is supplied and then stabilized. This is preferable, because most of the chromogens are water-insoluble and therefore it is necessary to add separately. Better reproducibility can be obtained by preparing the analytical element wherein the chromogen and the other reagents are previously incorporated into the prescribed layer.

4. Analytical Element Containing Mordant:

In the case that the coloring reagent forms an ionic dye, a mordant layer may be provided between the water-impermeable support and the reagent layer. The efficiency of optical detection can be improved by transferring the dye produced in proportion to the quantity of analyte in a sample to the mordant layer and trapping it there.

For example, in the case of forming a cationic dye by coloring reagents, a hydrophilic polymer layer containing a polymer having an anionic atom or atomic group bound to the polymer chain can be used as the mordant layer. In the case of forming an anionic dye by coloring reagents, a hydrophilic polymer layer containing a polymer having a cationic atom or atomic group bound to the polymer chain can be used.

The mordant polymers are described in detail in Japanese Patent KOKOKU No. 2-30466, U.S. Pat. No. 4,042,335, U.S. Pat. No. 4,166,093, U.S. Pat. No. 4,144,306, etc.

For example, anionic mordant polymers are alkali hydrolyzate of methyl vinyl ether-maleic anhydride copolymer, alkali metal salt or alkaline earth metal salt of polystyrene-p-sulfonic acid, alkali metal salt or alkaline earth metal salt of a copolymer of styrene-p-sulfonic acid and hydrophilic vinyl monomer, and the like disclosed at columns 13–14 of Japanese Patent KOKOKU No. 2-30466. The Japanese patent further discloses layers capable of incorporating the above polymers at columns 15–16.

5. Analytical Element having a Layer Construction of the above 1–4 Provided with Light-Shielding Layer Between Hydrophilic Polymer Layer and Spreading Layer:

Whole blood samples can be used as wihtout removing the microporous layer formed of fluorine-containing polymer containing surfactant. The light-shielding layer is a water-permeable layer where particulates having light-shielding ability or light-shielding ability and light-reflecting ability are dispersed in and supported by small amount of a hydrophilic polymer binder having film-forming ability. The light-shielding layer shields the color of an aqueous liquid sample, particularly red color of hemoglobin contained in a whole blood sample, when the detectable change (color change, coloring, etc.) is measured by reflection photometry from the light-transmissive support side, and also functions as a light-reflecting layer or a background layer.

Particulates having light-shielding ability and light-reflecting ability include titanium deoxide particulates (microcrystalline particulates having a particle size of about 0.1 μm to about 1.2 μm in rutile-type, anatase-type or brookite type, etc.), barium sulfate particulates, aluminum particulates and microflakes, and particulates having light-shielding ability include carbon black, gas black and carbon particulates. Among them, titanium dioxide particulates and barium sulfate particulates are preferred.

As the hydrophilic polymer binder having film-forming ability, there are the aforementioned hydrophilic polymers, and regenerated cellulose, cellulose acetate and the like which are weakly hydrophilic. Preferred ones are gelatin, gelatin derivatives, polyvinyl alcohol, polyacrylamide, maleic acid copolymers and the like. In the case of gelatin and gelatin derivatives, a known hardening agent (crosslinking agent) may be added.

6. Analytical Element having a Layer Construction of the Above 1–4 Provided with Water-impermeable Gas-permeable Layer (Barrier Layer) Between Hydrophilic Polymer Layer and Spreading Layer:

This analytical element is effective for the analysis of BUN (urea nitrogen) and CRE (creatinine) evolving ammonia gas, $CO_2$, etc. Either of whole blood and plasma can be used as samples. The barrier layer applicable to the invention includes the uniform coating layer of an uniform polymer disclosed in U.S. Pat. No. 4,066,403, membrane filter disclosed in U.S. Pat. No. 4,548,906 and the like.

7. Analytical Element having a Layer Construction of the Above 1–6 from which Spreading Layer is Remove, i.e. Microporous Layer is used also as Spreading Layer:

In all-of the above elements, the microporous layer may be substantially fixed with or may be in a peelable state from the adjacent layer. Particularly, in the case of whole blood samples, the microporous layer is preferably in the peelable state except the layer constructions having the light-shielding layer.

The measuring reagent means the reagent which directly reacts with analyte which is the subject to be analyzed to produce a chemical change. That is, in the case that an enzyme is analyte, the measuring reagent is a substrate thereof, and in the case that analyte is an antigen (antibody), it is an antibody (antigen). In the case that analyte is a lipid, a sacharide or a metabolite and a detectable change is produced by an enzyme, the measuring reagent is the enzyme. In the case that the above reactions are induced by a general chemical reaction caused by a chemical reagent other than enzyme, it is the corresponding chemical substance. Examples are shown below:

In the case that analyte is GOT, the measuring reagent is aspartic acid and α-ketoglutaric acid) and in the case of amylase, it is starch having a high molecular weight or origosaccharide having a low molecular weight. In the case of GGT, it is L-Γ-glutamylparanitro anilide, and in the case of ALP, it is paranitrophenyl phosphate. In the case of glucose, it is glucose oxidase, and in the case of uric acid, it is uricase, In the case of cholesterol, it is cholesterol esterase or cholesterol oxidase, in the case of neutral fats, it is lipase or esterase, etc. In the case that an indicator directly reacts with analyte, such as protein, albumin, Ca, inorganic phosphorus, etc. it is the indicator.

Since an object of the invention is to prevent degradation of the detecting reagent during stock which is a defect of conventional analytical elements, if a reaction reagent incorporated into the analytical element is unstable, such as some enzymes, the reaction reagent is preferably incorporated into the measuring reagent solution. That is, with respect to the distribution between the reagents to be incorporated into the measuring reagent solution and those to be incorporated into the analytical element, it may be varied using analytical performance and stock stability as an indicator. In the case of one analyte, the above distribution differs according to the construction of detecting reaction system.

Various reagents may be incorporated into the measuring reagent solution in order to adjust pH or ion strength so that reaction proceeds stably to obtain a good reproducibility, in order to improve diffusion and permeation into the materials constructing the analytical element, in order to improve the unstability of enzyme, etc. contained therein, or the like. Reagents for inhibiting reactions competitive to the detecting reaction may also be incorporated. As such a reagent, there are bilirubin oxidase, ascorbate oxidase, etc. Furthermore, a compound inhibiting an enzyme derived from a certain organism, such as an inhibitor of p-type amylase, may be added in order to detect an isozyme. In the case of measuring whole blood samples, $NaN_3$ or the like may be added which is effective as the inhibitor of catalase activity of hemoglobin.

In view of manufacturing, packaging, transportation, store, measuring operations, etc., the multilayer analytical element of the invention is preferably cut into square or circular pieces having a side or diameter of about 15 mm to about 30 mm, and put in a slide frame as disclosed in Japanese Patent KOKAI No. 57-63452, U.S. Pat. No. 4,169, 751, U.S. Pat. No. 4,387,990, PCT application WO 83/00391, etc. for use. However, it may be formed into a stick similar to urine test paper, etc.

In the case that the period from the supply of a liquid sample to the supply of measuring reagents is long, it is preferred that the analytical element is dried for a fixed time under substantially fixed conditions after the supply of a liquid sample. Preferable drying meth ds and conditions are disclosed in detail in Japanese Patent KOKAI No. 3-289543 from page 25, line 9 to page 28, line 6, particularly from page 27, line 13 to page 28, line 6. Preferable incubation methods and conditions are disclosed in the specification of Japanese Patent Application NO. 2-90562 from page 25, line 9 to page 28, line 6, particularly page 27, line 13 to page 28, line 6. A particularly preferred method is heating the analytical element is placed in an enclosure so that the circumference of the analytical element is covered. By employing this method, substantially constant dried state can be obtained without the influence of environmental temperature and moisture. A suitable temperature range is 10 to 60° C., preferably 20 to 45° C., more preferably 30 to 40° C. A suitable temperature variation through the incubation is ±5° C., preferably ±3° C., more preferably ±1° C.

An incubator suitable for the above incubation which is carried out under substantially fixed conditions is disclosed in Japanese Utility Model KOKAI No. 3-126499. The incubator is composed that an analytical element is placed in its receiving portion, heated by a heating means, and kept at a constant temperature. The incubator is provided with a detachable cover which can seal the element-receiving portion at the upper part of the receiving portion, and the volume of the space formed in the element-receiving portion closed by the cover is designed so as to almost conform to the volume of the analytical element. Similar good reproducible results can be obtained by blowing dried air with a fixed temperature under substantially fixed conditions, but this method is disadvantageous because of expensiveness compared with the above incubator.

Hereupon, "dried" is in the state that reactions substantially do not proceed or that degradation of analyte does not proceed. Therefore, it is different according to analyte, and for example, in the case of enzymes, moisture content in the hydrophilic polymer is less than 50%, preferably less than 20%, more preferably less than 10%.

In the case that the period from the analytical element which was stabilized to the supply of the measuring reagent solution is long, for example, in the case that the analytical element is mailed to a hospital or the like, the analytical element is necessary to be kept in the conditions substantially excluding moisture and air. The details of the preservation are also disclosed in Japanese Patent KOKAI No. 3-289543 from page 28, line 12 to page 30, line 11. For example, a means is of sealing the analytical element in a box made of metal or a bag made of a water-impermeable organic polymer or metal film or sheet provided with a moisture-removing means. As the moisture-removing means, a moisture absorbing agent which substantially does not denature the analyte is selected from known ones, and placed it. Another means to get out the air in the bag by wiping sufficiently after the analytical element is put therein.

The analysis using the aforementioned dry analytical element is conducted by the following method. To the analytical element taken out from the above sealed container, the measuring reagent solution corresponding to the analytical item is supplied. Reaction occurs, and the analyte contained in the sample is determined by measuring the reaction using a known method (reflection photometry, color change, fluorometry, emission photometry, etc.) in the dry analysis method. If necessary, the microporous layer formed of fluorine-containing polymer containing surfactant may be removed.

As the measuring reagent solution, a known reagents solution in the wet analysis can be used. The reagents react with the analyte to produce a change, mainly a change detectable by an optical measuring method, such as color change, coloring, fluorescence, luminescence, absorption wave length change in ultraviolet region, generation of turbidity, etc.

As the measuring method in the dry analysis, reflection optical system is usually employed. In the method of the invention, the photometry conducted through the water-impermeable support of the analytical element has the widest application range. However, in the case that the sample is not whole blood or that measurement is conducted after removing the microporous layer, the measurement can be conducted by measuring transmitted light. When the water-impermeable support is opaque, the measurement can be conducted from the side opposite to th support.

The preservation of the dry analytical element in the invention can be utilized in every field corresponding to the aforementioned Groups 1 through 3, and it is also effective in the clinical medical assay in the inspection at home.

In the case that blood is used as the sample, since dry analytical elements need a very small amount of blood, blood can be drawn by using a suitable device such as a capillary pipette. When the dry analytical element is applicable to whole blood, the blood drawn can be used as the liquid sample for measuring as it is, and therefore, the element is particularly effective for the inspection at home system. When the dry analytial element is for plasma or serum, plasma or serum is separated from the blood drawn by centrifuging or standing, and used as the liquid sample for measuring. Body fluids other than blood, such as urine and saliva, a suitable amount is placed in a container, and directly used as the sample.

The above samples are supplied to the dry analytical element used in the invention, preserved according to the method of the invention, transported if necessary, and analysis by the method mentioned previously. It is possible to transport by mail or courier, and sufficiently applicable to the inspection at home system.

Figure 1:
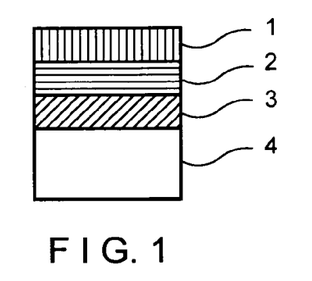
FIGS. 1 through 8 are partially sectional views of analytical elements which are applicable to the invention.
Figure 2:
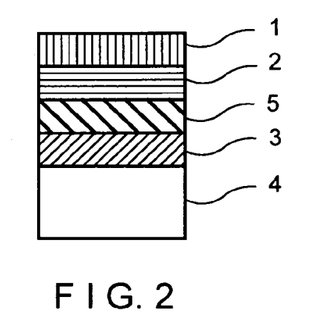
Figure 3:
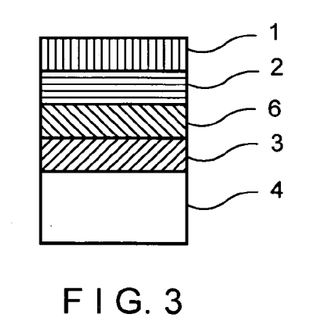
Figure 4:
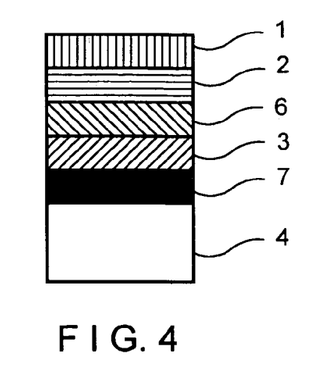
Figure 5:
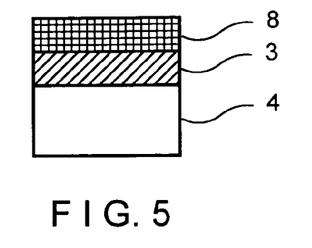
Figure 6:
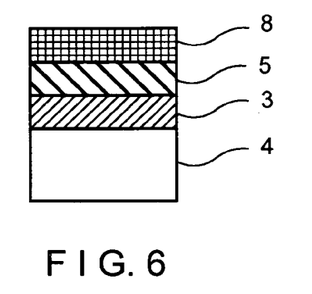
Figure 7:
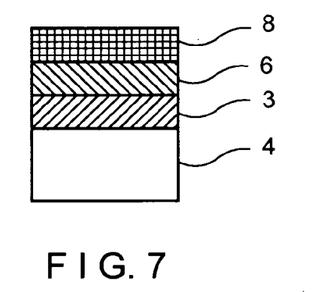
Figure 8:
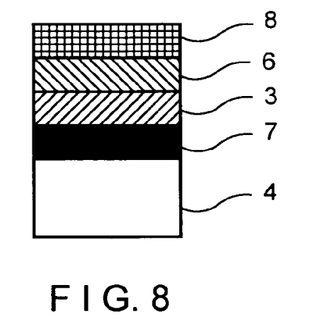
Figure 9:
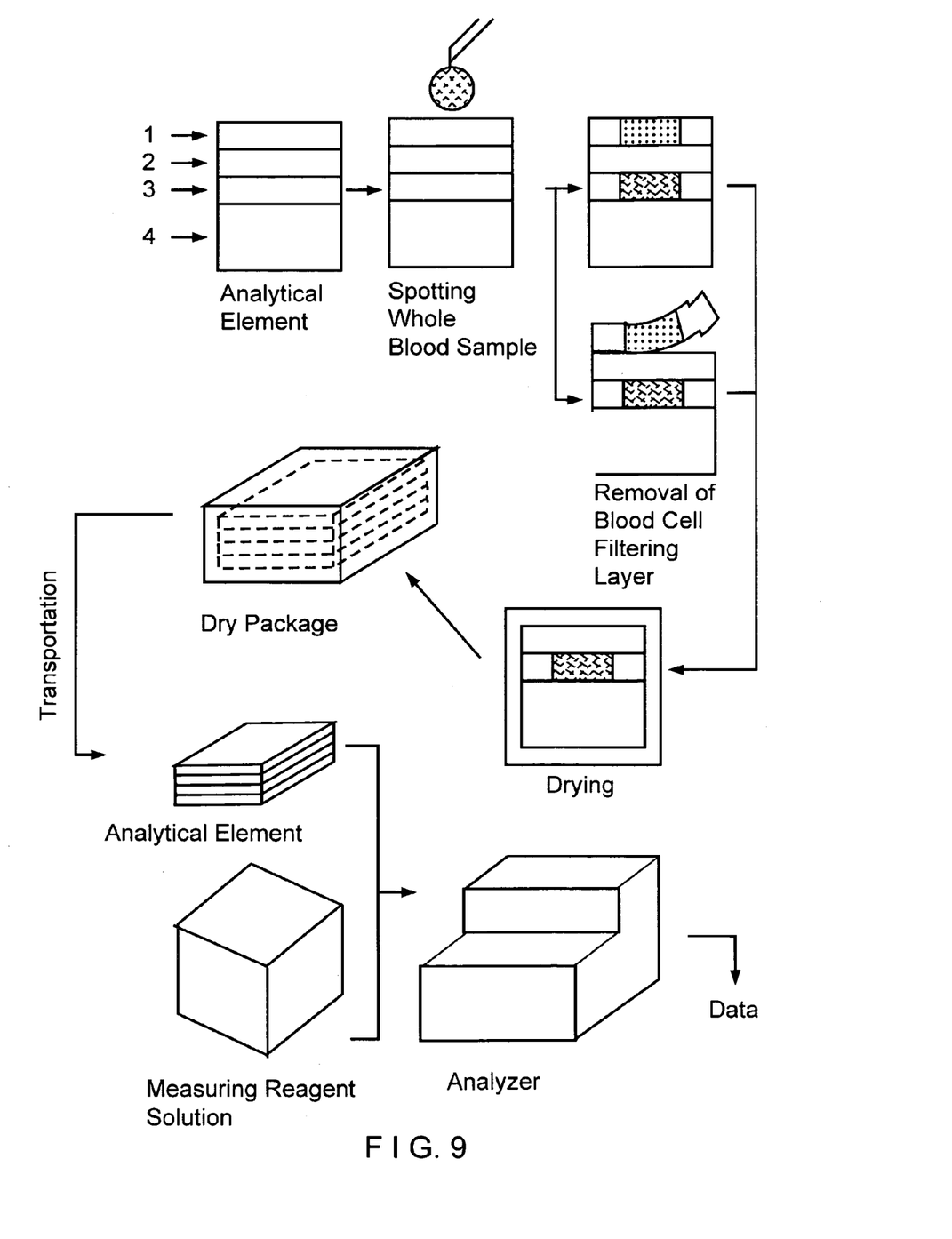
FIG. 9 is a schematic illustration indicating a procedure of the invention.

A procedure of the method of the invention is shown in FIG. 9. The analytical element is composed of a blood cell filtering layer 1, a spreading layer 2, a hydrophilic polymer layer 3 and a support 4 laminated in this order, and measuring reagents are not incorporated. A whole blood sample is spotted onto the blood cell filtering layer 1 of the analytical element, and the blood cell filtering layer is left as it is or peeled off. Then, the analytical element is dried to dehydrate, and packed in a package capable of keeping the dried state. The package is transported, and the analytical element is set in an automatic analyzer together with the measuring reagent solution. Then, analysis is conducted, and the result is obtained.

Since the dry analytical element used in the invention does not contain unstable measuring reagents, the shelf life is greatly improved compared with conventional dry analytical elements. Besides, since the measuring reagents used in the conventional wet analysis can be used, it is not necessary to develop analytical elements for each measuring item. Moreover, one kind of analytical element can be applied to many items, and therefore, it is inexpensive.

EXAMPLES

Example 1

① Preparation of Analytical Element

Onto a transparent film base of polyethylene terephthalate 180 $\mu$m in thickness provided with undercoating for gelatin, gelatin containing 0.2% of nonionic surfactant p-nonylphenoxypolyglycidol (containing 10 glycidol unit on average) was applied so that the dry thickness was about 15 $\mu$m, and dried. Polyester knitted fabric which was made hydrophilic by using surfactant was laminated thereonto according to the method disclosed in Japanese Patent KOKAI No. 62-224299. 7% polyvinylpyrrolidone (mean molecular weight: 1,200,000) ethanol solution was applied onto the spreading layer so that the coating amount was 2 g/m².

② Hydrophilic Treatment of Fluorine-containing Polymer

A polycetrafluoroethylene microporous membrane ("Zitex A135", Norton, USA) was immersed in an ethanol solution containing 20% of Triton X-150. Air contained in micropores of the membrane was removed, and the surfactant solution was sufficiently permeated into the micropores. Then, the membrane was taken out of the solution, and dried by blowing dried air at 50° C.

③ The analytical element prepared in ① was cut into square pieces in a size of 15 mm×15 mm. The fluorine-containing microporous membrane rendered hydrophilic in ② was also cut into square pieces in a size of 15 mm×15 mm, and superposed on the spreading layer of the above analytical element. Each superposed one was placed in a plastic mount according to the method disclosed in Japanese Patent KOKAI No. 57-63452 to complete an analytical element.

④ Preparation of GGT Measuring Reagents Solution

To 10 ml of 10 mM tris buffer solution at pH 8.1, 10 μl of Triton X-100, 156 mg of glycylglycin and 5.9 mg of L-Γ-glutamyl-3-carboxy-4-nitroanilide were dissolved to prepare a GGT measuring reagent solution.

⑤ Spotting of Sample

A whole blood sample drawn from a healthy person with heparin was divided into 3 test tubes in an amount of each 2 ml, and to No. 2 and No. 3 test tubes, 10 μl and 20 μl of a saline solution containing 10,000 U/l of GGT were added.

Each 20 μl of the above whole blood samples in 3 concentration levels was spotted onto ③ pieces of the analytical element prepared in 3 per each concentration level using a micropipette. The whole blood was permeated into the side of the microporous membrane together with extending on the membrane. After about 10 seconds, it was confirmed that the diffusion entirely proceeded, and then, the microporous membrane was removed by using a pincette.

⑥ Incubation

The analytical element was then warmed to dryness at 37° C., for 10 minutes in an opened state, according to the method disclosed in Japanese Patent KOKAI No. 3-289543.

⑦ Measurement

The analytical elements obtained in the above ⑥ were set in "Fuji Dry Chem 5500" analyzer (Fuji Photo Film Co., Ltd.). The measuring reagent solution prepared in ④ was sucked into a pipetting apparatus, and spotted. Each analytical element was incubated, and then, reflection optical density was measured at the wave length of 400 nm according to usual measuring perations. The difference between the density after 1 minute from the spotting of the measuring reagent solution and that after 5 minutes was calculated.

Separately, the whole blood sample prepared in ⑤ was centrifuged, and GGT activity of the plasma was measured by using "Hitachi 7050" analyzer.

⑧ Result

The relationship between a mean value of ΔODR measured according to the method of the invention and the enzyme activity value measured by "Hitachi 7050" analyzer is shown below.

| Sample | No. 1 | No. 2 | No. 3 |
|---|---|---|---|
| $\Delta OD_R$ | 0.027 | 0.102 | 0.188 |
| GGT Activity (U/l) | 35 | 238 | 433 |

As shown above, it was confirmed that both are in a good proportionality.

Example 2

① Preparation of Analytical Element

An analytical element was prepared similar to Example 1 except that a gelatin layer containing 1 g/m² of leucoallylimidazole, 20,000 U/m² of peroxidase and 0.5% of Triton X-100 per gelatin was coated as the reagent layer instead of the gelatin layer containing 0.2% of nonionic surfactant (p-nonylphenoxypolyglycidol).

② Preparation of Whole Blood Sample Containing Choresterol 10 ml of vein blood drawn from a healthy person with heparin was pipetted into 4 test tubes of No. 1 to No. 4 in an amount of each 1.5 ml.

Separately, Fuji Dry Chem control sera CP-L, CP-M and CP-H were dissolved in each 1.5 ml of distilled water.

Each 1.5 ml of CP-L, CP-M or CP-H was added to the test tubes Nos. 2, 3, 4 and mixed to prepare whole blood samples No. 1 to No. 4 different in total cholesterol concentration. A part of them was taken, centrifuged, and measured by "Hitachi 7050" analyzer to obtain the results of No. 1: 126 mg/dl, No. 2: 93 mg/dl, No. 3: 183 mg/dl, No. 4: 265 mg/dl.

③ Preparation of Measuring Reagent Solution

The reagent solution having the following recipe was prepared.

| | |
|---|---|
| Choresterol esterase | 987 U |
| Choresterol oxidase | 600 U |
| Triton X-100 | 500 mg |
| 50 mM phosphate buffer (pH 7.5) | 10 ml |

④ Spotting of Sample

Each 20 μl of the whole blood samples prepared in ② was taken by a micropipette, and spotted onto each three pieces of No. 1 to No. 4 of the analytical elements prepared in ①, i.e. 12 pieces in the total. After about 10 seconds from the spotting, the microporous membrane was peeled off.

⑤ Drying Treatment

Similar to Example 1 moisture content was dried and removed by keeping the analytical element at 37° C. for 10 minutes.

⑥ Measurement

Using "Fuji Dry Chem 5500", similar to Example 1, the measuring reagent solution was spotted, and reflection optical density was measured at 650 nm after 6 minutes.

⑦ Result

The measured results are shown below.

| Sample | No. 1 | No. 2 | No. 3 | No. 4 |
|---|---|---|---|---|
| $\Delta OD_R$ (average of n = 3) | 0.493 | 0.462 | 0.563 | 0.622 |
| Measured Value of TCHO (mg/dl) | 126 | 93 | 183 | 265 |

As can be seen from the above results, there was a good relationship between the reflection optical density measured by the method of the invention and the total cholesterol value of the plasma measured by "Hitachi 7050".

Example 3

① Preparation of Analytical Element

A dispersion mixture of $TiO_2$ and gelatin was applied onto the gelatin coating layer of Example 2 so chat the coating amount was 10 g/m², and dried. Further, the plasma-separating membrane which was a constituent of "CHEM- CARD" (Chematic, USA) was peeled off and superposed onto the above film to prepare an analytical element similar to Example 1.

② Preparation of Measuring Regent Solution

The measuring reagent solution having the following recipe was prepared.

| Glucose oxidase | 2,000 U |
|---|---|
| 0.1M MES buffer (pH 5.7) | 10 ml |
| Triton X-100 | 10 µl |
| NaN$_3$ | 20 mg |

③ Preparation of Whole Blood Containing Glucose

Using blood of a healthy person drawn in a blood drawing tube containing heparin and NaF, 4 kinds of whole blood samples different in glucose concentration were prepared by adjusting glucose.

④ Spotting of Sample, Drying

10 µl of the sample prepared in ③ was spotted onto the analytical element prepared in ①, and subsequently dried at 37° C. for 10 minutes.

⑤ Measurement

Similar to Example 1, reflection optical density after 6 minutes was measured at 510 nm using "Fuji Dry Chem 5500".

⑥ Result

The results are shown below.

| Sample | No. 1 | No. 2 | No. 3 |
|---|---|---|---|
| Measured Value by Hitachi 7050 (mg/dl) | 69 | 146 | 295 |
| Reflection Optical Density (OD$_R$) by Method of the Invention | 0.272 | 0.364 | 0.491 |

From the above results, it can be seen that there is a good relationship between the reflection optical density according to the method of the invention and the results measured using "Hitachi 7050".

Subsequently, the glucose concentration of No. 4 sample was calculated from the measured result using the above relationship, and found to be 108 mg/dl. On the other hand, the same sample was centrifuged, and the glucose concentration of the plasma was measured by "Hitachi 7050", and found to be 111 mg/dl. Thus, it was seen that the results obtained by the method of the invention were reliable.

Example 4

① Preparation of Analytical Element

Onto a transparent polyethylene terephthalate film 180 µm in thickness having an undercoating, gelatin containing 0.2% of nonionic surfactant (p-nonylphenoxypolyglycidol) and 1% of leucoallylimidazol was applied in a dry thickness of about 15 µm, and dried. The plasma-separating membrane which was a constituent of "CHEMCARD" (Chematic, USA) was peeled off and superposed onto the coating layer. The closely superposed matter was incorporated into the plastic mount similar to Example 1 to complete an analytical element.

② Preparation of Measuring Reagent Solution

Similar to Example 3, a measuring reagent solution was prepared.

③ Preparation of Whole Blood Containing Glucose

Similar to Example 3, 3 kinds of samples different in glucose concentration were prepared. A part was taken, centrifuged, and glucose concentration of the plasma was measured.

④ Spotting of Sample, Drying

10 µl of the sample prepared in ③ was spotted onto the analytical element prepared in 1, and dried at 37° C. for 10 minutes.

⑤ Spotting of Measuring Reagent Solution

10 µl of the measuring reagent solution prepared according to the following recipe was spotted onto the analytical element dried in ④, and incubated at 37° C. for 6 minutes.

| Glucose oxidase | 2,000 U |
|---|---|
| Peroxisase | 1,200 U |
| 0.1M MES buffer (pH 5.7) | 10 ml |
| Triton X-100 | 10 µl |
| NaN$_3$ | 20 mg |

Immediately after the incubation, the microporous membrane of fluorine-containing polymer was peeled off, and transmission optical density of the anlaytical element was measured using a Macbeth transmission densitometer.

⑥ Result

The relationship between the glucose concentration of the plasma measured by "Hitachi 7050" and the transmission optical density measured in ⑤ in shown below. It can be seen from the results that there is a good relationship between both values and that glucose concentration of whole blood can quantitatively measured by the method of the invention.

| Sample | No. 1 | No. 2 | No. 3 |
|---|---|---|---|
| ΔOD$_R$ | 0.03 | 0.07 | 0.11 |
| Glucose Concentration in Plasma (mg/dl) | 35 | 238 | 433 |

Example 5

A dry analytical element was dried similar to Example 3, except that the spreading layer was peeled off after 1 minute from the spotting of the whole blood sample and then the analytical element was incubated.

Subsequently, a porous layer made of polyester knitted fabric rendered newly hydrophilic was closely placed onto the analytical element. The measuring reagent solution was spotted thereonto, and measured by "Fuji Dry Chem 5500".

Similar to Example 3, the relation between the glucose concentration value of the plasma measured by "Hitachi 7050" and the reflection optical density after 6 minutes was almost a straight line.

Example 6

Figure 10:
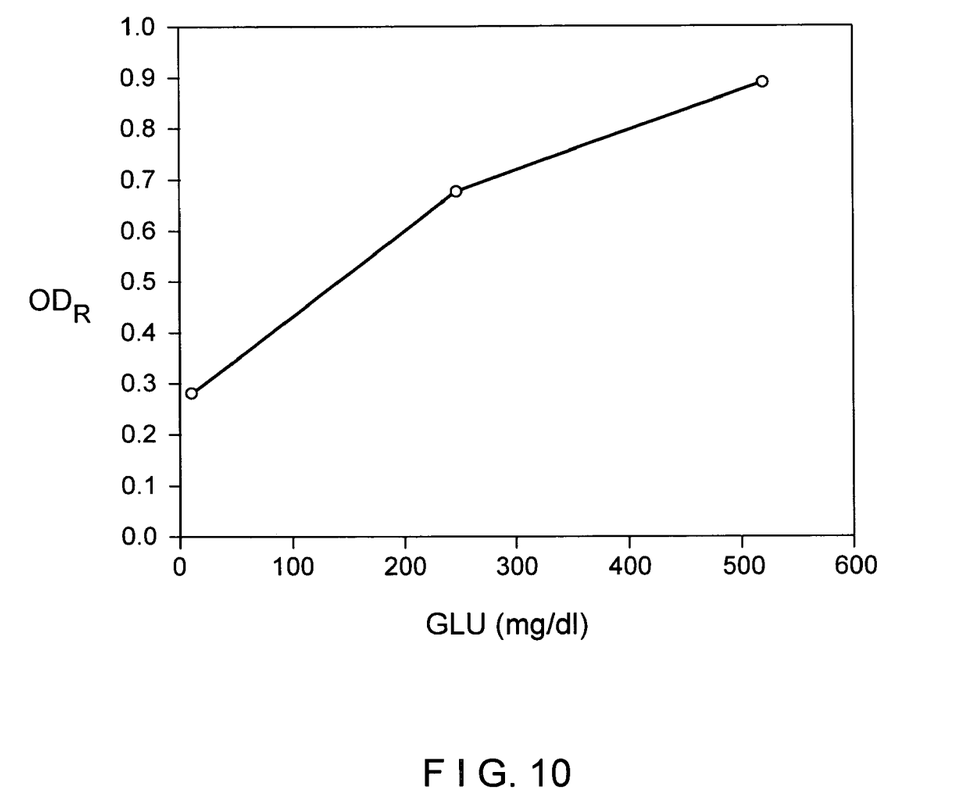
FIG. 10 is a graph indicating a relation between the glucose concentration of a sample measured by the solution method and reflective optical density.

Evaluations were conducted similar to Example 3, except that plasma obtained by centrifuging whole blood was used as the sample. The results are shown in FIG. 10. From the results, it can be seen that there is a good relationship between both values.

Example 7

① Preparation of Analytical Element

Onto a transparent polyethylene terephthalate film 180 μm in thickness having undercoating, polyvinyl alcohol ("KL 506", Kurare) containing 0.2% of nonionic surfactant p-nonylphenoxypolyglycidol (containing 10 glycidol units on average) blended with epoxy compound ("Araldite DY 022", Ciba-Geigy) as crosslinking agent was coated in a dry thickness of about 15 μm, and dried. Thereonto, a polyester knitted fabric rendered hydrophilic was laminated according to the method disclosed in Japanese Patent KOKAI No. 62-224299. Further thereonto, an ethanol solution containing 1.5% of hydroxyethyl cellulose ("HPC", Shin-Etsu Chemical) and 0.25% of nonionic surfactant ("HS 240", Nippon Oil and Fats) for the purpose of controlling spreading was applied in an amount of 250 g/m², and dried.

② Preparation of Blood Cell Separating Element

Polytetrafluoroethylene microporous membrane of which the surface and the inner surface of pores were rendered hydrophilic by a hydrophilic polymer 1 "Poreflon WPW-100-100", Sumitomo Denko) was cut into discs 12 mm in diameter. Separately, glass fiber filter paper ("CA-55", Advantec) was cut into discs 8 mm in diameter. Plastic single face adhesive tape was punched into discs 15 mm in diameter having a circular window 6 mm in diameter at the center, and thereonto, the above microporous membrane disc and glass fiber filter paper disc were adhered disposing the glass fiber filter paper on the adhesive cape side.

③ Assembling of Analytical Element for Whole Blood

The coated film prepared in the above ① was cut into square piece 15 mm×15 mm in size, and it was incorporated into a plastic mount (longitudinal: 28 mm, lateral: 24 mm, thickness: 1.5 mm) made of high impact polystyrene having a window 10 mm in diameter at the center to prepare the analytical element having the same figure as disclosed in Japanese Patent KOKAI No. 57-63452. The blood cell separating element prepared in the above ② was adhered to the analytical element at the position so that the microporous membrane contacted closely the spreading layer of the analytical element and so that the center was consistent to the center of the window, and fixed to complete an analytical element for whole blood.

④ Preparation of Measuring Reagent Solution for Measuring Total Protein

The following reagent composition was dissolved in 20 ml of water to prepare a measuring reagent solution utilizing the biuret reaction.

| | |
|---|---|
| Copper sulfate (5 hydrates) | 3.5 g |
| Tartaric acid | 2.3 g |
| Lithium hydroxide | 3.8 g |
| Cetylmethylammonium bromide | 0.1 g |

⑤ Preparation of Sample

A whole blood sample drawn from a healthy person with heparin was divided into 3 test tubes No. 1–No. 3 in an amount of each 2 ml, end a small amount of borrine serum albumin was added to No. 2 and No. 3 test tubes to prepare whole blood samples different in total protein concentration. A part of them was centrifuged, and total protein concentration of the plasma samples was determined by using "Hitachi 7050".

⑥ Spotting of Sample

Each 30 μl of the whole blood samples prepared in ⑤ was spotted onto the analytical element prepared in the above ③. The whole blood first rose in drop on the glass fiber filter paper, and gradually permeated into the under layers. After leaving the element for 1 minute from spotting the whole blood, an edge was the adhesive tape was pinched by a pincette, and the blood cell separating element was peeled off the plastic slide mount. It was confirmed that only plasma was transferred to the coated film fixed to the plastic slide mount in a circle about 10 mm in diameter.

⑦ Dehydration of Separated Plasma

The dry analytical element which received the plasma obtained in ⑥ was placed in an aluminum heating block of which the temperature was set at 37° C., and dehydrated and dried by leaving for 5 minutes, according to the method disclosed in Japanese Patent KOKAI No. 3-289543.

⑧ Measurement of Total Protein

The analytical element obtained in ⑦ was set in "Fuji Dry Chem 5500" analyzer (Fuji Photo Film Co., Ltd.). 10 μl of the measuring reagent solution prepared in ④ was sucked by a pipetting apparatus, and spotted according to usual measuring operations. After incubating for 6 minutes, reflection optical density was measured at 540 nm.

⑨ Preparation of Calibration Curve

Each of the whole blood samples different in protein concentration prepared in ⑤ were measured three times, and a calibration curve was prepared using the reflection optical density values and the measured values of "Hitachi 7050".

Measurement of Simultaneous Reproducibility

As to samples different from the whole blood samples of ⑤, repeating measuring accuracy was examined by repeating the operations of ⑥ to ⑧ 10 times, and the following results were obtained.

| | |
|---|---|
| Mean value: | 7.4 g/dl |
| SD: | 0.13 g/dl |
| CV: | 1.8% |

By the experiment, it was confirmed that the present method has a sufficient quantitativeness.

Example 8

① Assembling of Analytical Element for Whole Blood

An analytical element for whole blood was prepared similar to Example 7, except that a polysulfone microporous membrane 2 μm in pore size 150 μm in thickness was used instead of the polycetrafluoroethylene microporous membrane of which the surface was rendered hydrophilic by the hydrophilic polymer in Example 7-②.

② Preparation of GGT Measuring Reagent Solution

| | |
|---|---|
| Glycylaglycin | 156 mg |
| L-α-glutamyl-3-carboxy-paranitroaniline | 58.5 mg |
| 15 mM Tris-HCl buffer (pH 8.1) | 10 ml |

③ Preparation of Sample

Vein blood drawn from a healthy person with heparin was divided into 3 test tubes in an amount of each 2 ml. Each 200 μl of plasma was removed from No. 2, No. 3 samples, and the same volume of calibrator CP-M, CP-H solutions for Fuji Dry Chem dissolved in 1 ml of saline solution to prepare whole blood samples different in enzyme concentration. A part of the No. 1 to No. 3 samples thus prepared was taken, centrifuged, and GGT activity of the plasma samples was measured by using "Hitachi 7050" analyzer.

④ Measurement of GGT Activity of Whole Blood Sample by the Method of the Invention The slide was treated and the activity was measured according to the same operation procedure as ⑥–⑨ of Example 7. However, in ⑧ measuring wave length was 400 nm, measuring time was 5 minutes, and the variation of, reflection optical density with time was the difference from 5 minute value to 1 minute value.

⑤ Measurement of Simultaneous Reproducibility

As to samples different from the whole blood samples used above, repeating measuring accuracy was examined by repeating the operations of ⑥ to ⑧ of Example 7 10 times, and the following results were obtained.

| | |
|---|---|
| Mean value: | 17 U/l |
| SD: | 1.5 U/l |
| CV: | 8.8% |

It was confirmed that the present method has a quantitativeness.

Example 9

An analytical element was prepared similar to Example 7 wherein the blood cell separating element was changed to the filter paper for filtering blood cells "Cyto Step #1661-012" (R. Strom).

When 40 μl of vein blood drawn from a healthy person with heparin was spotted, plasma could be filtered onto the slide in good conditions.

Example 10

① Preparation of Analytical Element

An analytical element was prepared according to Example 1-①. Furthermore, the solution for spread control similar to Example 5-① was applied onto the spreading layer, and dried to prepare and anlaytical element.

② Preparation of Analytical Element for Whole Blood

An analytical element was prepared similar to Example 7-②, ③.

③ Preparation of GPT Measuring Reagent Solution 50 mg of 2-(3,5-dimethoxy-4-hydroxyphenyl)-4-[4-(dimethylaminophenyl]-5-phenethylimidazol and 200 mg of Triton X-100 (trade name) were added to the measuring reagent solution of Example 2-③ to prepare the measuring reagent solution.

④ Preparation of Sample

Whole blood samples No. 1–No. 3 different in GPT activity were prepared similar to Example 8-③.

⑤ Measurement of GPT Activity

Slides were treated, and GPT activity was measured according to the same operation procedure as Example 7-⑥-⑨. However, the measuring conditions of the analyzer were at the wave length of 640 nm for the measuring time of 5 minutes, and the difference of 5 minute value to 1 minute value was used.

⑥ Measurement of Simultaneous Reproducibility

As to the same whole blood sample as above, repeating measuring accuracy was examined by repeating the above procedure ⑤ times, the following results were obtained.

| Sample | No. 1 | No. 2 | No. 3 |
|---|---|---|---|
| Mean value (U/l) | 18 | 286 | 728 |
| SD (U/l) | 0.68 | 9.2 | 19.7 |
| CV (%) | 3.8 | 3.2 | 2.7 |

What is claimed is:

1. A method for quantitatively measuring an analyte using a dry analytical element which comprises:
   A) supplying a whole blood sample to be analyzed to an analytical element comprising layers comprising at least a hydrophilic polymer layer and a microporous layer having a surface rendered hydrophilic and being laminated onto a water-impermeable support in the order of the microporous layer, the hydrophilic polymer layer, and then the support, said microporous layer being capable of separating blood cells; said whole blood sample being supplied onto said microporous layer;
   B) drying the analytical element from step A for a fixed time period within a range of ±5° C. of a fixed drying temperature, wherein said fixed drying temperature is within the range of 10–60° C., to obtain a moisture content of the hydrophilic polymer of less than 20%;
   C) pipetting a measuring reagent solution above the microporous layer to the dried analytical element from step B to cause a reaction to occur corresponding to an analyte in the blood sample, said measuring reagent reacting directly with the analyte to produce a chemical change;
   D) removing the microporous layer, and
   E) subjecting the analytical element from step D to optical measurement to analyze the analyte in the whole blood sample.

2. The method of claim 1 wherein the analytical element comprising at least a water-impermeable gas-permeable layer which is provided between the hydrophilic polymer layer and the microporous layer.

3. The method of claim 2 wherein said microporous layer is formed of fluorine-containing polymer or polysulfone.

4. The method of claim 2 wherein said analytical element further comprises a porous spreading layer provided between the microporous layer and the hydrophilic polymer layer.

5. The method of claim 1 wherein the analytical element further comprises a light-shielding layer which is provided between the hydrophilic polymer layer and the microporous layer.

6. The method of claim 5 wherein said microporous layer is formed of fluorine-containing polymer or polysulfone.

7. The method of claim 5 wherein said analytical element further comprises a porous spreading layer provided between the microporous layer and the hydrophilic polymer layer.

8. The method of claim 1 wherein said microporous layer is formed of fluorine-containing polymer or polysulfone.

9. The method of claim 1 wherein said analytical element further comprises a porous spreading layer provided between the microporous layer and the hydrophilic polymer layer.

10. The method of claim 1 wherein the drying is conducted at 30 to 40° C.

11. The method of claim 4 wherein the drying is conducted in an incubator composed of an element-receiving portion, a heating means, a cover which seals the element-receiving portion at the upper part of the receiving portion, and the volume of the space formed in the element-receiving portion closed by the cover is designed so as to almost conform to the volume of the analytical element.

12. The method of claim 1 wherein the moisture content of the hydrophilic polymer is less than 10% after dried.

13. The method of claim 1 further comprising transporting the dry analytical element after the liquid sample is supplied.

14. The method of claim 13, wherein the dried analytical element is transported to a hospital.

15. The method of claim 1 applied to the clinical medical assay in order to monitor clinical conditions of patients at home.

16. The method of claim 1 wherein the analyte is an enzyme.

17. The method according to claim 1 wherein said measuring reagent solution contains a surfactant.

18. A method for quantitatively measuring an analyte using a dry analytical element which comprises:
A) supplying a whole blood sample to be analyzed to an analytical element comprising layers comprising at least a hydrophilic polymer layer and a microporous layer having a surface rendered hydrophilic and being laminated onto a water-impermeable support in the order of the microporous layer, the hydrophilic polymer layer, and then the support, said microporous layer being capable of separating blood cells; said whole blood sample being supplied onto said microporous layer;
B) drying the analytical element from step A for a fixed time period within a range of ±5° C. of a fixed drying temperature, wherein said fixed drying temperature is within the range of 10–60° C., to obtain a moisture content of the hydrophilic polymer of less than 20%;
C) pipetting a measuring reagent solution above the microporous layer to the dried analytical element from step B to cause a reaction to occur corresponding to an analyte in the blood sample, said measuring reagent reacting directly with the analyte to produce a chemical change; and
D) subjecting the analytical element from step C to optical measurement to analyze the analyte in the whole blood sample.

* * * * *